(12) United States Patent
Smith et al.

(10) Patent No.: US 11,567,944 B2
(45) Date of Patent: Jan. 31, 2023

(54) PROCESSING OF SEQUENCING DATA STREAMS

(71) Applicant: GARVAN INSTITUTE OF MEDICAL RESEARCH, New South Wales (AU)

(72) Inventors: Martin Smith, New South Wales (AU); James Ferguson, New South Wales (AU); Dennis Bunadi, New South Wales (AU)

(73) Assignee: GARVAN INSTITUTE OF MEDICAL RESEARCH, New South Wales (AU)

( * ) Notice: Subject to any disclaimer, the term of this patent is extended or adjusted under 35 U.S.C. 154(b) by 263 days.

(21) Appl. No.: 16/497,146

(22) PCT Filed: Mar. 23, 2018

(86) PCT No.: PCT/AU2018/050265
§ 371 (c)(1),
(2) Date: Sep. 24, 2019

(87) PCT Pub. No.: WO2018/170552
PCT Pub. Date: Sep. 27, 2018

(65) Prior Publication Data
US 2020/0110752 A1    Apr. 9, 2020

(30) Foreign Application Priority Data

Mar. 24, 2017  (AU) ................................. 2017901072
Nov. 2, 2017   (AU) ................................. 2017904458

(51) Int. Cl.
*G06F 16/00*   (2019.01)
*G06F 16/2455* (2019.01)
(Continued)

(52) U.S. Cl.
CPC .......... *G06F 16/24568* (2019.01); *G06F 9/54* (2013.01); *G06F 16/22* (2019.01);
(Continued)

(58) Field of Classification Search
CPC combination set(s) only.
See application file for complete search history.

(56) References Cited

U.S. PATENT DOCUMENTS 6,553,317 B1 * 4/2003 Lincoln .................. G16B 50/30
                                            435/6.12
10,309,968 B2 * 6/2019 Tran ........................ G16B 30/10
(Continued)

FOREIGN PATENT DOCUMENTS

WO   2016/059427 A1   4/2016

OTHER PUBLICATIONS

International Search Report and Written Opinion issued in PCT/AU2018/050265, dated May 4, 2018, 5 pages.
Loose, et al., 'Real-time selective sequencing using nanopore technology', Nature Methods, Sep. 2016, vol. 13, Issue 9, pp. 751-754. Section "Abstract", "Dynamic Time Warping" (18 pages).
(Continued)

*Primary Examiner* — Farhan M Syed
(74) *Attorney, Agent, or Firm* — Kilpatrick Townsend & Stockton LLP

(57) ABSTRACT

This disclosure relates to methods and systems for processing of sequencing data streams. The system receives sequences from a sequencer and stores them as data records on a database. The sequences are associated with a counter indicative of a number of times the associated sequence has been sequenced. The system progressively receives a further sequence as streaming data from the sequence. While receiving the further sequence, the system matches the streaming data against the stored sequences to determine a matching score. Upon the matching score exceeding a matching
(Continued)

threshold for one of the multiple sequences in the database, the system selects the one of the sequences in the database based on the matching score and stores the further sequence on non-volatile memory where the counter value associated with the selected sequence is below a saturation threshold. The system also terminates the receiving where the counter value is above the saturation threshold.

17 Claims, 5 Drawing Sheets

(51) Int. Cl.
  *G16B 30/10* (2019.01)
  *G06F 16/22* (2019.01)
  *G06F 16/2457* (2019.01)
  *G06F 9/54* (2006.01)
  *G06F 16/2458* (2019.01)
(52) U.S. Cl.
  CPC .... *G06F 16/2474* (2019.01); *G06F 16/24578*
    (2019.01); *G16B 30/10* (2019.02)

(56) References Cited

U.S. PATENT DOCUMENTS

| | | | | |
|---|---|---|---|---|
| 2004/0024535 | A1* | 2/2004 | Lincoln | G16B 50/10 |
| | | | | 702/20 |
| 2007/0038381 | A1* | 2/2007 | Melchior | G16B 30/00 |
| | | | | 702/19 |
| 2011/0270533 | A1* | 11/2011 | Zhang | G16B 30/20 |
| | | | | 702/20 |
| 2015/0066385 | A1* | 3/2015 | Schnall-Levin | G16B 30/20 |
| | | | | 702/20 |
| 2016/0124966 | A1* | 5/2016 | Cohen | H04L 63/145 |
| | | | | 707/723 |
| 2017/0336419 | A1* | 11/2017 | Tran | G16B 30/00 |

OTHER PUBLICATIONS

Extended European Search Report in Application No. 18772385.3, dated Nov. 3, 2020, 11 pages.
Jain et al., 'The Oxford Nanopore MinION: delivery of nanopore sequencing to the genomics community', Genome Biology, Nov. 25, 2016, vol. 17 (1), 11 pages.

* cited by examiner

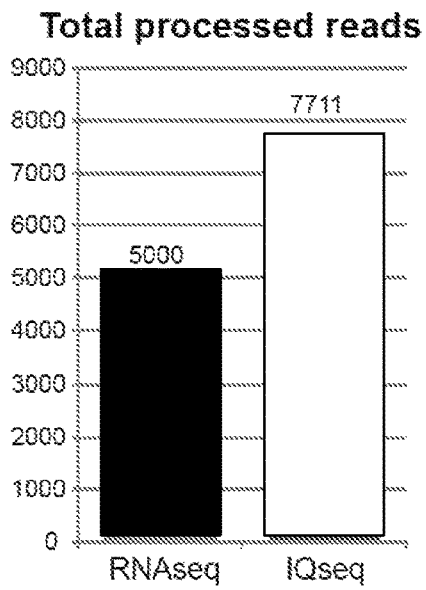
Fig. 6a
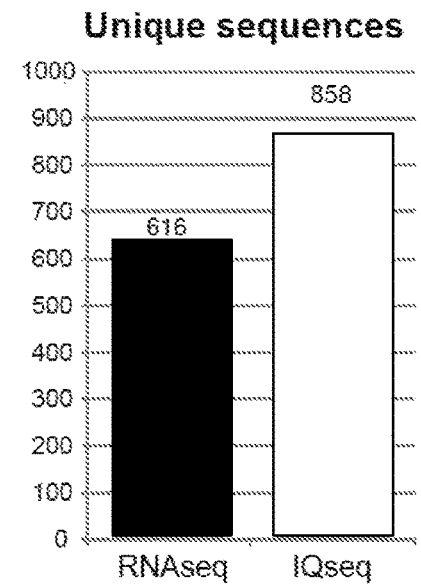
Fig. 6b
| Indexed Sequence ID | RNAseq | IQseq |
|---|---|---|
| 1 | 1187 | 1822 |
| 5 | 146 | 226 |
| 25 | 32 | 51 |
| 100 | 5 | 7 |
| 500 | 1 | 1 |
| 617 | 0 | 1 |
| 858 | 0 | 1 |
Indexed sequence counts
Fig. 6c
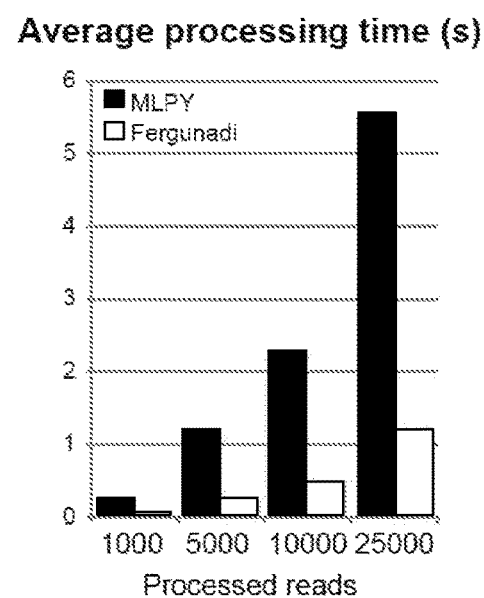
Fig. 6d

PROCESSING OF SEQUENCING DATA STREAMS

CROSS-REFERENCE TO RELATED APPLICATIONS

The present application is a U.S. National Stage of International Application No. PCT/AU2018/050265 filed on 23 Mar. 2018, which claims priority from Australian Provisional Patent Application No. 2017901072 filed on 24 Mar. 2017 and Australian provisional application 2017904458 filed on 2 Nov. 2017. Each of these applications is hereby incorporated for reference in its entirety for all purposes.

TECHNICAL FIELD

This disclosure relates to methods and systems for processing of sequencing data streams. In particular, but not limited to, this disclosure relates to processing data streams from nanopore sequencers.

BACKGROUND

Measuring the abundance and variation of unique molecules in biological systems can serve to identify cellular states, environmental responses, and progression of pathologies. Experimental quantification of molecular concentrations using sequencing techniques is limited by sampling depth. Indeed, highly abundant molecules can mask the presence of molecules in low concentration given the finite sampling depth or time of most methods. Detecting low abundance molecules is important because they can have different functions or discriminative characteristics. For example, 'housekeeping' proteins or RNAs are often highly abundant, whereas regulatory macromolecules are expressed at weaker levels, making them more difficult to characterise when sampling stochastically. Regulatory molecules have more important or drastic roles and provide unique information about cellular dynamics, for instance.

Nanopore sequencing offers new applications that were previously impossible. In particular, the availability of a stream of sequencing data allows real-time processing of the sequencing data. However, it is a challenge to process the stream of sequencing data to derive a meaningful conclusion while the stream is received. This challenge mainly arises from the large amount of noisy data that needs to be matched against a potentially large set of references. Currently, this excessive processing time limits the application of real time analyses using nanopores. This problem is expected to grow as nanopore sequencers with increasing numbers of parallel pores come onto the market.

SUMMARY

The present disclosure provides a method for processing streaming data from a sequencer, such as a nanopore. A database stores sequences previously received from the sequencer together with counters for each stored sequence. While the streaming data is received, a processor matches the streaming data progressively against the stored sequences. As soon as a match is found, the processor checks the counter of the matching sequence. If the counter is below a threshold, the processor keeps the current sequence but if the counter is above the threshold, the processor stops receiving the sequence and proceeds to the next sequence.

A method for processing streaming data from a sequencer comprises:
receiving multiple sequences from the sequencer;
storing each of the multiple sequences as data records on a database, each of the multiple sequences being associated with a counter indicative of a number of times the associated sequence has been sequenced;
progressively receiving a further sequence as streaming data from the sequencer;
while receiving the further sequence, matching the streaming data against each of the multiple sequences in the database to determine a matching score for each of the multiple sequences in the records of the database;
upon the matching score exceeding a matching threshold for one of the multiple sequences in the database, selecting the one of the multiple sequences in the database based on the matching score;
storing the further sequence on non-volatile memory where the counter value associated with the selected sequence is below a saturation threshold; and
terminating the receiving of the further sequence where the counter value associated with the selected sequence is above the saturation threshold.

It is a technical advantage that the selectively storing and rejecting allows for filtering the sequences by abundances in real time. As a result, the overall hard disk storage requirements are reduced because the most abundant sequences (above saturation threshold) are rejected. At the same time, the least abundant sequences (below saturation threshold), which are of the main interest, are stored for further analysis.

Terminating the receiving of the further sequence may comprise sending a reject signal to the sequencer to abort sequencing the further sequence before the sequencer reaches the end of the further sequence and to allow a next sequence to be sequenced before the further sequence is fully sequenced.

Storing the sequence as data records in the database may be conditional on the matching score being below the matching threshold for the sequences stored in the database.

Storing the sequence as data records in the database may comprise storing a digital representation of an electric signal received from the sequencer.

Matching the streaming data may comprise matching a digital representation of an electric signal indicative of the further sequence against the digital representation of the electric signal stored on the database.

Determining a matching score may comprise performing dynamic time warping.

Performing dynamic time warping may comprise selectively calculating cells in an associated dynamic programming matrix that are within a specified range or value.

The method may further comprise upon the matching score exceeding a matching threshold for one of the multiple sequences in the database incrementing the counter for the one of the multiple sequences.

Matching the streaming data may comprise matching the streaming data against a subset of the multiple sequences in the database, wherein the subset is based on the counter.

The subset may include sequences for which the associated counter is above an abundance threshold.

It is a technical advantage that the computational complexity can be reduced by limiting the matching to a subset of the stored sequences. Importantly, this subset includes the most abundant sequences (above the abundance threshold) which are exactly those sequences that should be rejected. This way, the matching can be performed at a speed that matches the rate of sequences generated by the sequencer.

The sequencer may comprise a nanopore.

The method may further comprise:

monitoring the counters in the database to determine whether one or more counters exceed a depth threshold; and upon determining that one or more counters exceed a depth threshold, creating an alert that sufficient sequences have been sequenced.

The data records may form an associative array, each record may comprise a key/value pair and the value may comprise the sequence and the counter.

Receiving the multiple sequences may comprise using an application programming interface (API) to receive the multiple sequences.

Storing the sequence as data records in the database may comprise storing a digital representation of a nucleic acid sequence.

The method may further comprise performing base calling on the further sequence while receiving the further sequence.

Determining the matching score may comprise performing sequence alignment or comparison.

A computer system for processing streaming data from a sequencer comprises:

a data port to receive multiple sequences from the sequencer;

a database to store each of the multiple sequences as data records on a database, each of the multiple sequences being associated with a counter indicative of a number of times the associated sequence has been sequenced;

a processor to:
- while progressively receiving a further sequence as streaming data from the sequencer, match the streaming data against each of the multiple sequences in the records of the database to determine a matching score for each of the multiple sequences in the records of the database
- upon the matching score exceeding a matching threshold for one of the multiple sequences in the database, select the one of the multiple sequences in the database based on the matching score;
- store the further sequence on non-volatile memory where the counter value associated with the selected sequence is below a saturation threshold; and
- terminate the receiving of the further sequence where the counter value associated with the selected sequence is above the saturation threshold.

Optional features described of any aspect of method, computer readable medium or computer system, where appropriate, similarly apply to the other aspects also described here.

BRIEF DESCRIPTION OF DRAWINGS

An example will now be described with reference to:

FIG. 6a shows the number of reads processed using the proposed method compared to a prior art method.

FIG. 6b shows the number of unique sequences identified using the proposed method compared to a prior art method.

FIG. 6c illustrates the coverage achieved using the proposed method compared to prior art methods.

FIG. 6d illustrates average processing times.

DESCRIPTION OF EMBODIMENTS

Figure 1:
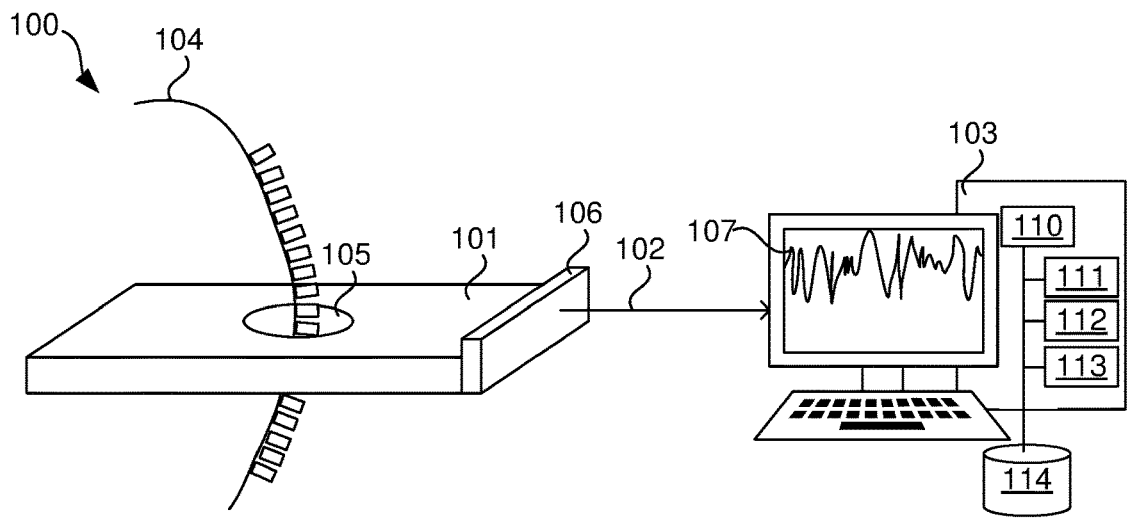
FIG. 1 illustrates a sequencing system.

There is a need for reducing the processing time that is currently required in the processing of streaming data from a sequencer, such as a nanopore including the MinION device by Oxford Nanopore Technologies. In some applications, a small number of different sequences constitute the majority of reads. For example, in RNA sequencing, a small number of housekeeping RNA constitutes a majority of reads but in most cases, the most frequent sequences are of little interest. This is particularly the case when expression levels are to be measured for research or clinical diagnosis. In that case, a minimum coverage should be reached for the minority sequences. However, a large number of reads for housekeeping RNA often needs to be generated in order to reach an acceptable coverage for the less frequent, but more relevant sequences. This leads to excessively long sequencing times, which leads to increased cost for occupying the sequencer and for reagents.

This disclosure provides a method for Squiggle QUantification InDex sequencing (SQUIDseq), a data acquisition method that expands sampling depth while simultaneously quantifying molecular abundances. SQUIDseq is method that aims to reduce the redundancy of sequencing experiment outputs and increase the depth, breadth, and diversity of sequenced molecules while preserving molecular abundance information.

The solution disclosed herein addresses the issue of exceeding processing time by dynamically building a database of sequences and gradually determining the most frequent sequences. The database can then be used to match the sequencing data as it is received against the database and terminate acquisition of the most frequent reads before they reach the end of the read. This way, the next read can be processed earlier than if each read was processed entirely. It is noted that different databases may be used, which includes external databases hosted by a database management system, such as relational (e.g. SQL) databases, graph databases (e.g. CouchDB) as well as internal databases that are maintained in programming variables and form internal data structures, such as lists, arrays, sets, heaps, stacks, dictionaries, distributed hash tables, etc. As such, the database may be stored on and accessed from hard disk or may be stored on and accessed from RAM. Storing the database entirely on RAM increases speed but limits the database size and increases the risk of data loss due to a system crash.

It is noted that the terms 'read' and 'sequence' are used interchangeably herein. Generally, the term 'read' is used to describe the signal, data or result from a single molecule received by the nanopore or the single molecule itself. As such, two reads can be identical, similar or different. In contrast, the term 'sequence' is used to describe a unique signal, data or result. As such, any two sequences should be different. However, as will be described in more detail below, this is not always an exact statement as the equality of two sequences is not always determined. As a result, two reads may be stored as two sequences although they are identical, for example.

FIG. 1 illustrates a sequencing system 100 comprising a sequencer 101 generating streaming data 102 and a computer 103 for processing the streaming data 102. In use, the read 104—such as a DNA, RNA, or peptide macromolecule—passes through a pore 105. An electronics interface 106 of the pore 105 measures the electric properties across the pore, such as current, voltage, conductance, etc. For simplicity, this disclosure uses the electric current as an example. Each of the different bases has a different atomic charge configuration and therefore influences the current across the pore 105 differently. As a result, the electric current changes as the different bases pass through the pore 105. The electronics interface 106 records this current and generates a signal indicative of that current.

The term streaming data may refer to this 'raw' signal that directly reflects the current across the pore. In another example, the electronics interface 106 pre-processes the current signal into a compressed form, which is referred to as a 'squiggle'. In general terms, a squiggle represents the normalised values of current signal over time where periods of constant or comparable current are eliminated for data reduction. Computer system 103 displays an example squiggle 107. It is noted that in most examples, the squiggle is stored as a digital signal, such as an array or list of digital values, such as 8-bit values. More detailed information can be found in Hengyun Lu, Francesca Giordano, Zemin Ning: "Oxford Nanopore MinION Sequencing and Genome Assembly", Genomics Proteomics Bioinformatics 14 (2016) 265-279, which is included herein by reference.

In yet another example, the streaming data is the 'raw' signal and computer system 103 performs base calling on the fly to convert the raw sequence data into a stream of bases. For example, computer system 103 reduces the raw data into base-space by a general purpose processor (CPU), graphics processor (GPU) or dedicated hardware. Computer system 103 then performs the methods described herein but instead of using squiggles, computer system 103 uses the base-space signal. In one example, the base-space signal is a sequence of the four letters ACGT, which may be encoded by binary numbers 00, 01, 10 and 11, for example. Other encodings, such as one hot (0001, 0010, 0100, 1000) may equally be used.

Computer system 103 comprises a processor 110 connected to program memory 111, volatile data memory 112, such as RAM, non-volatile data memory 113, such as a hard disk, as well as a database 114. Computer system 103 may comprise a CPU, GPU, FPGA, Integrated Circuit, or other hardware with data processing and storage capability in place or in addition to processor 110. For example, computer system 103 may be implemented within a USB stick with a dedicated embedded electronics hardware for performing the methods described herein. In this case, electronics interface 106 linked to the sequencer may only provide limited preprocessing or simply perform basic analog signal amplification. In this case, the signal processing is mainly performed by the computer system 103, such as involving a GPU, CPU or FGA, for example.

The database may be fully or partially hosted on volatile memory 112, fully hosted on local non-volatile data memory 113, or externally. Program memory 111 stores a computer program that is installed on computer system 103 and that causes processor 110 to perform the method of FIG. 2. Computer system 103 may be implemented in a distributed computing environment, that is, on a cloud computing platform. In other examples, computer system 103 is a local server or personal computer. In particular, the latest nanopore sequencers are portable and suitable for use with laptop computers and even mobile phones. As it would be appreciated, these devices often have less computing resources than cloud-based architectures. For this reason, the proposed method can be particularly useful to reduce processing time on these constrained devices to allow fast quantitative expression level analysis, for example.

Figure 2:
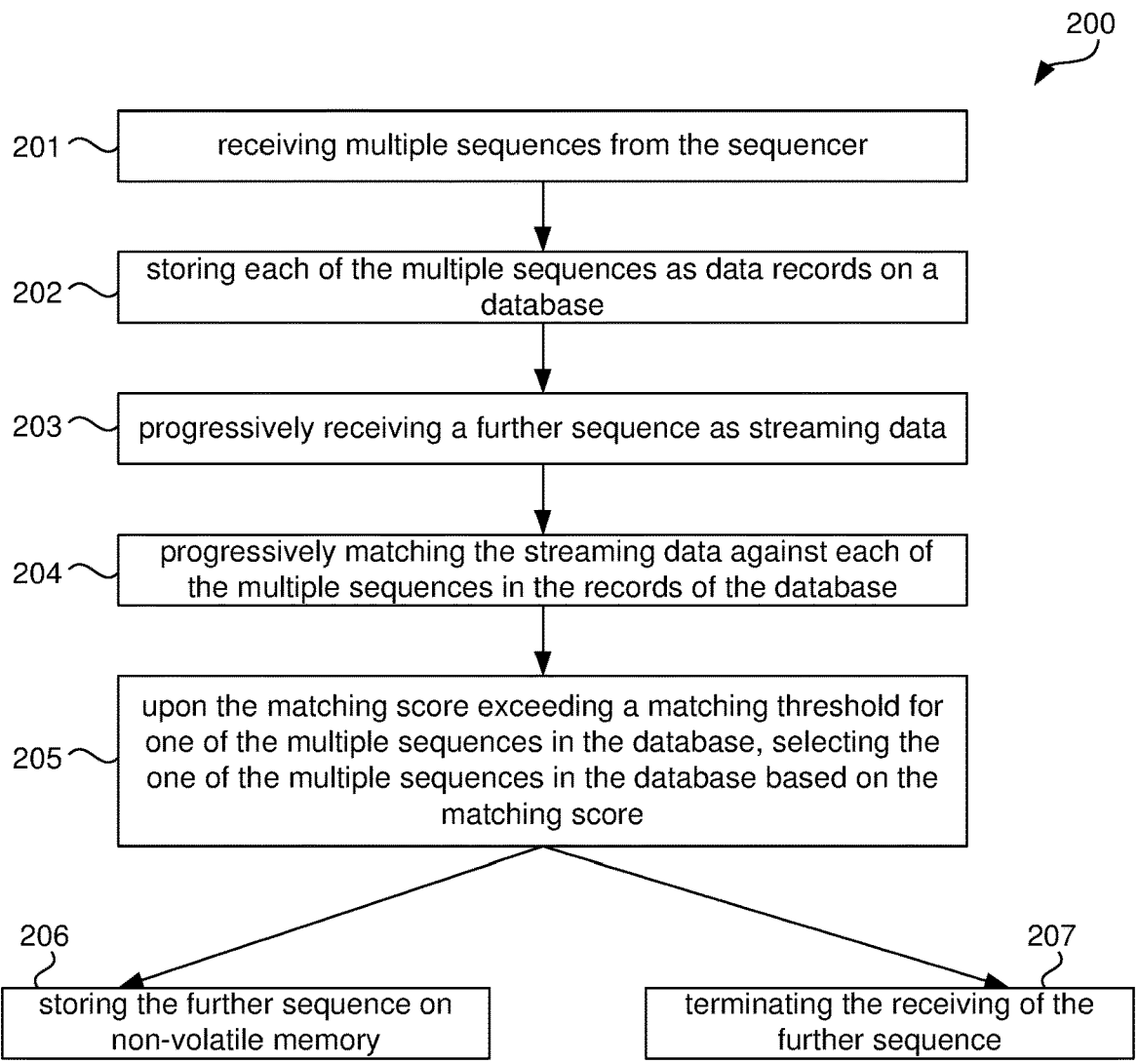
FIG. 2 illustrates a method for processing streaming data.

FIG. 2 illustrates a method for processing streaming data 102 from sequencer 101. First, processor 110 receives 201 multiple sequences from sequencer 101 and stores 202 each of the multiple sequences as data records on database 114.

Figure 3:
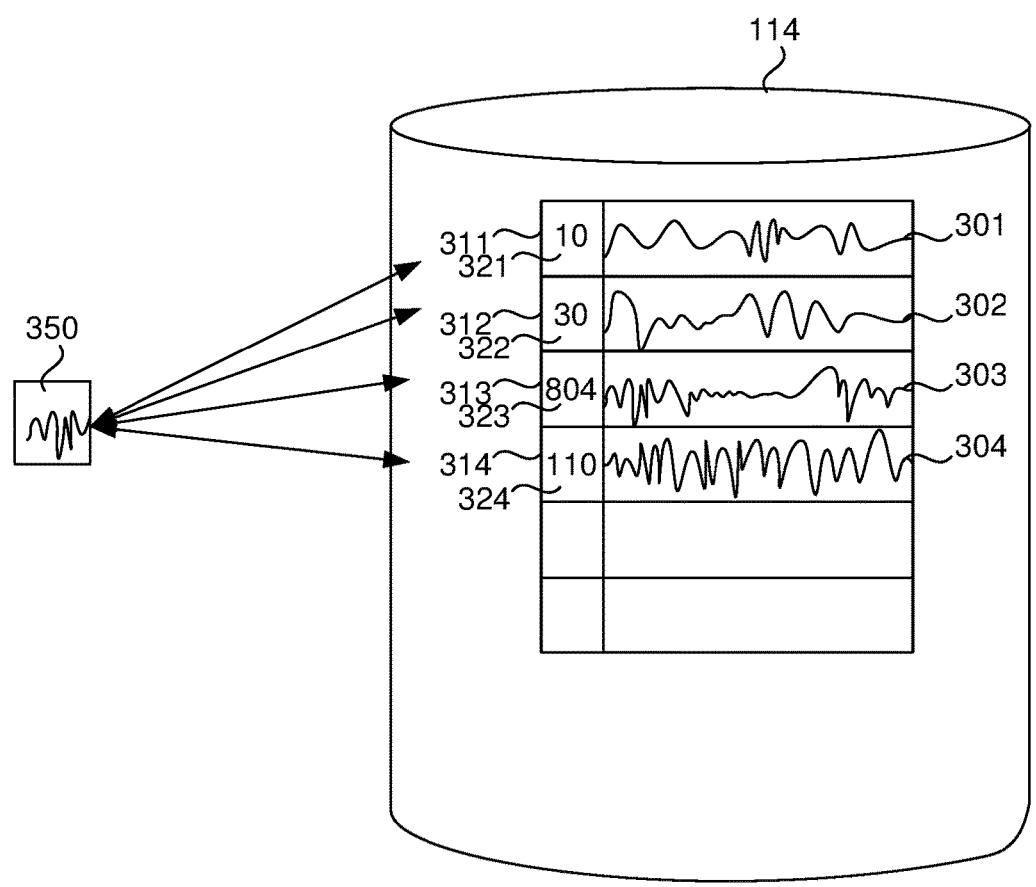
FIG. 3 illustrates the database from FIG. 2 in more detail.

FIG. 3 illustrates database 114 in more detail after each of the multiple sequences are stored on database 114. In this case, database 114 stores four sequences 301, 302, 303, 304 in four respective records 311, 312, 313, 314. In this example, the four sequences 301, 302, 303, 304 are stored in the form of respective squiggles. Further, each of the stored sequences is associated with a respective counter 321, 322, 323, 324. Each counter is indicative of a number of times the associated sequence has been sequenced. In this case, 954 reads were received from sequencer 101 for four different sequences. Accordingly, the counter values together add up to 954. For example, counter 323 has a value of 804, which means that the coverage of sequence 303 is already relatively high, that is, 804×.

Processor 110 then progressively receives 203 a further sequence as streaming data from the sequencer. Progressively in this context means that processor 110 has only the beginning part of the sequence available for processing and over time, more data becomes available. In other words, the squiggle gets longer and processor 110 processes the squiggle at the same time. In particular, while receiving the further sequence, processor 110 progressively matches 204 the streaming data against each of the multiple sequences in the records of the database. In the example of FIG. 3, processor 110 receives squiggle 350 and matches the beginning of the squiggle 350, that is the part of the squiggle that processor 110 has received so far, against each sequence in the database 114. That is, processor 110 matches squiggle 350 against squiggle 301, against squiggle 302, against squiggle 303 and against squiggle 304. Matching one squiggle against another may be achieved by processor 110 calculating a matching score. If the matching score is above a threshold, processor 110 decides that there is a match.

In one example, processor 110 continuously receives the squiggle and once a pre-defined amount of data is received, processor 110 performs the matching. The pre-defined amount may be between 100-1,000 events, such as 300 events, or data generated in 0.1-1 s, such as 0.3 s, or 500-10,000 raw data points, such as 1000 data points. In one example, the nanopore sequencer 101 generates 450 bases per second with an average RNA transcript of around 1kb, that is about 2 s of raw data per read. In this case, 0.3 s provides a good balance between matching accuracy versus reduction in time by ejecting the current read early. Accordingly, it is preferable that the pre-defined amount of data is less than the average read length. It is further preferable that the pre-defined amount of data is less than 50% of the average read length. It is also preferable that the pre-defined amount of data is more than 25% of the average read length.

Once the pre-defined amount of data is received, processor 110 matches the received squiggle against each squiggle 301, 302, 303 and 304 in the database. In the example of FIG. 3, there is now a match against third squiggle 303. That is, the matching score between received squiggle 350 and stored third squiggle 303 is above the matching score. In this sense, processor 110 calculates a matching score for each sequence 301, 302, 303, 304 in database 114 and continuously updates the matching score while processor 110 receives further streaming data.

When processor 110 determines that the matching score exceeds the matching threshold for one of the multiple sequences in the database, processor 110 selects 205 the one of the multiple sequences in the database based on the matching score. In the example of FIG. 3, it can be seen that received sequence 350 looks similar to third sequence 303, which is reflected by an above threshold matching score. As a result, processor 110 selects third sequence 303.

Processor 110 then branches into two different options based on the counter value. If the counter value is below a saturation threshold, processor 110 stores 206 the further sequence on non-volatile memory, such as in a read file on hard disk 113. Alternatively, if the counter value associated with the selected sequence is above a saturation threshold, processor 110 terminates 206 the receiving of the further sequence where the counter value associated with the selected sequence is above the saturation threshold. As a result, the further sequence is not stored on hard disk 113. This reduces the storage requirements on the hard disk 113 and makes the dataset more manageable for later use because the most frequent sequences are not overly represented. Further, the termination of receiving the sequencing data means that the next sequence can be received earlier than if all sequences are received entirely. As a result, the sampling of molecules is increased overall, allowing more of the less frequent sequences to be sequenced in a constant sequencing time, that is, without increasing the total number of sequenced reads.

The matching threshold may be specific to the method used by processor 110 to compare the received sequence to the database. It is noted that the matching threshold can be determined empirically from sequences of known composition, such as sequencing data from synthetic RNA molecules. This can be used to train a discriminative matching threshold at a given accuracy. An example of this is to compare 200 reads composed of 20 unique sequences against each other with a selected comparative method, then compare the resulting scores to a binary classification of identical versus non-identical sequences and select a value with optimal discriminative ability. A less stringent matching threshold will consider more divergent sequences as matches at step 205. This also means steps 206 and 207 occur more frequently. This reduces computational load on processor 110, reduces the size of the database 114, reduces the output sequencing data on non-volatile memory 113. As a potential downside, different sequences may be treated as the same more frequently. The result may by a loss in diversity of sequences saved to non-volatile memory. In an extreme case, only a specified number of sequences equivalent to the saturation threshold value will be saved. Conversely, a more stringent threshold will have the opposite effect, and in extreme instances will have no added benefit to a default sequencing procedure. An effective matching threshold is therefore advantageous to achieve optimal benefits.

Although the matching threshold is typically static for a selected comparative method, it is noted that this value can also be increased or decreased dynamically during a sequencing run or given certain conditions of the sequencing device 101 or the data stream 102. An example of why this may be of value is when the nature or quality of the sequencing data stream 102 varies progressively during a sequencing experiment. For example, the amount of noise in the signal can increase over time, as sequencing reagents or solutions are depleted. In this scenario, varying the matching threshold may increase specificity or sensitivity, as desired.

It is further noted that the early termination of receiving the sequence data reduces the processing time because the processor 110 matches less of the sequence against the stored sequences. This means, processor 110 can instead process streaming data from other channels/pores.

As mentioned above, processor 110 terminates the receiving of the further sequence in cases where the counter of the matched sequence is above the saturation threshold, which represents the maximal amount of sequences to be stored to the hard disk 113. A lower number, e.g. 20, ensures that the termination signal 207 will be reached faster for abundant sequences and will allow the sequencer to sample a broader diversity of molecules. Conversely, a higher number (e.g. 150) will output 206 more reads matching the same sequence 205 and facilitate the identification of subtle differences in sequence composition. In one example, the sequencing data is originally created by a sequencer, such as an Illumina×10 and stored on a server, and the server streams the sequencing data as a stream to computer system 103. In that example, processor 110 terminates the receiving of the streaming data by sending a termination message to the server or simply stopping the acknowledgment of the receipt of the streaming data. For sequencing samples with a broad diversity of molecules with different concentrations, increasing the saturation threshold will reduce the breadth of sequencing (amount of unique sequences) in favour of increasing the depth of sequencing (amount of similar or redundant sequences).

In other examples, particularly when a nanopore sequencer is used, processor 110 can send a reject signal to the sequencer. This aborts the sequencing of the further sequence before the sequencer reaches the end of the further sequence and allows a next sequence to be sequenced before the further sequence is fully sequenced. For example, electronics interface 106 can reverse the feed current to expel the current sequence out of the nanopore. It is noted that there is often a dead time of a few seconds before the nanopore 105 receives the next sequence. However, it is noted that this dead time will rarely occur simultaneously at multiple nanopores, which means the remaining nanopores continue creating sequencing data and the overall amount of data processed by processor 110 is not significantly reduced by one nanopore being inactive.

In some examples, a software installed on computer system 103 writes a temporary data file to hard disk 113 while receiving the data stream. In that case, terminating the receiving also involves deleting the temporary data file or allowing the temporary data file to be overwritten by the streaming data for the next sequence.

Steps 201 and 202 are presented above as initialisation steps to fill the database 114 with sequences from the sequencer at the beginning of the sequencing. It is noted, however, that processor 110 may store further sequences in the database. In particular, in cases where the matching scores for the sequences that are already stored are below the matching threshold, processor 110 stores the current sequence on database 114. This can be generalised for the very first sequence that is received. At the very beginning, the database 114 is empty, which means that no sequence in database 114 matches the received stream. As a result, the streamed sequence is added as a new record in database 114. Processor 110 then receives the second sequence and matches it against the first sequence. If it doesn't match, processor 110 adds the second sequence as a new record in database 114 and so on. This means that even after 10,000 sequences have been received and processed, processor 110 may receive a new sequence that matches against none of the previously stored sequences. In that case, processor 110 adds the new sequence as a new record on database 114. In other words storing the sequence as data records in the database is conditional on the matching score being below the matching threshold for the sequences stored in the database.

While some examples may store the entire sequence, it is noted that storing only a part of the sequence, that is a sub-sequence, can further reduce the size of database 114 without significantly reducing the resulting data quality. The sub-sequence may be the beginning of the sequence, which is adequate because processor 110 matches the received stream against the beginning of the stored sequences. Although it is possible that two sequences match at the beginning but are different at the rest of the sequence, such occurrences are relatively uncommon in biological systems, which is the reason why the quality of resulting data remains high. In one example, the length of the stored sequence is 250 events sequentially spanning positions 50 to 300 of the streaming data 102. In another example, the raw electronic current values between 0.05 to 0.4 seconds after commencing receipt of the streaming data 102 are stored into database 114 instead of the normalised (squiggle) data. In RNA sequencing, the beginning of a sequence is defined by the 3' end of the sequence and the nanopore is configured to receive this end first. In other examples, however, there may be ambiguity over which end is the beginning (such as cDNA sequencing where both extremities present double stranded DNA). In that case, database 114 may store two entries for each sequence, which are the parts from ether of the two ends. This avoids storing the middle of the sequence, which could potentially be 90% of the sequence that is not stored on database 114. It is noted that the full sequence is still stored on hard disk 113 for later analysis but is not being used for matching.

It is noted that the sequences can be stored in the database as a digital representation of the electric signal received from the interface 106 of sequencer 101. In one example, the digital representation is a squiggle where a series of raw values is replaced by a single entry or event. In another example, a sliding average window can be applied to the raw electric signal to bypass the generation of the squiggle. Again, this reduces the overall number of data points, which decreases processing time due to the smaller number of comparisons to perform in step 205 of method 200.

It is now apparent that matching the streaming data comprises matching a digital representation of an electric signal indicative of the further sequence against the digital representation of the electric signal stored on the database. In one example, processor 110 performs this matching by performing dynamic time warping (DTW), which can readily deal with sequences that are created with different speeds of the molecule 104 moving through the pore 105. Examples include the use of PrunedDTW, SparseDTW, and the FastDTW.

DTW has a broad range of applications but for this particular application of matching digital representations of an electric signal, DTW—a dynamic programming algorithm—can be further accelerated. In general, the cell pointers and backtracking stage of the algorithm, which returns the optimal path or alignment of both signals, can be bypassed as the nature of the alignment is not essential to the proposed method. More particularly, DTW calculates a distance matrix or grid where each cell indicates the distance between a position in the stored sequence (row) and a position in the streamed sequence (column), added to the cumulative distance of the local minima of the 3 previous cells (row−1, column), (row, column−1); or (row−1, column−1). In that sense, the calculation of columns in each row "far" from the minima column of the previous row can be skipped in order to reduce computational load and decrease processing time. Therefore, certain cells of the distance matrix are less relevant than others since they generally do not cause the matching score to reach the threshold. In other words, processor 110 selectively calculates elements of the grid that positively contribute to a matching score. One example of this is to only calculate the cells within proximity of the diagonal of the matrix. This way, processor 110 may reduce the number of cells to decrease processing times. Another example would consist of only calculating cells of the distance matrix where the 3 previous cells are below a given value, as 'daughter' cells cannot be lesser than any of the previous 3. The given value can be a function of or equal to the matching threshold, as only sequences that satisfy this threshold will be considered by method 205.

In examples where the most abundant sequences are yet to be identified, processor 110 increments the counter for the matching sequence once a match is identified. Processor 110 may increment the counter in cases where the counter is below the saturation threshold and also in cases where the counter is already above the saturation threshold. The main difference between these two cases is that processor 110 stores the streamed sequence in the database 114 in the former case and terminates the receiving in the latter case. In other examples, however, processor 110 does not increment the counter if the counter is already at the saturation threshold.

It may be appreciated that the processing time for matching the streamed sequence against all records in database 114 grows with the number of stored sequences. While this may not be a major concern at the beginning of the sequencing where the number of sequences is low, it may prevent processor 110 from processing the streaming data 102 at the same or higher rate as the sequencer 101 generates the data. As a result, there would be a backlog, which significantly reduces the advantages of early termination of the receiving of streaming data. In order to keep up with the data generation, processor 110 may match the streaming data against a subset of the multiple sequences in the database. This subset may be based on the counter. For example, processor 110 may order the sequences by counter values and match only against the top 10 or top 100. In other examples, processor 110 matches against sequences with a counter value above an abundance threshold, which may be equal to the saturation threshold. However, the abundance threshold may also be different to the saturation threshold.

As a result, the subset includes the most abundant sequences (above the abundance threshold) which are exactly those sequences that should be rejected. This way, the matching can be performed at a speed that matches the rate of sequences generated by the sequencer. As a potential downside, processor 110 may not detect that a received sequencing stream would match against one of the less abundant sequences. As mentioned above, this may lead to two identical reads stored as sequences on database 114. In many applications, however, it is valuable to retain multiple reads of the less abundant sequences, so the potential downside is often not relevant.

It is noted that the abundance threshold may be adjusted automatically. For example, the abundance threshold may be adjusted based on the processor load or based on the number of stored sequences or both. In some examples, processor 110 monitors the counters in the database to determine whether one or more counters exceed a depth threshold. When one or more counters exceed a depth threshold, processor 110 creates an alert that sufficient sequences have been sequenced. In that event, the sequencing can be stopped altogether by the user or automatically by the processor 110.

In order to make data access more efficient, the data records may form an associative array. Each record may then comprise a key/value pair and the value comprises the sequence and the counter. The key may be a hash value of the squiggle, which means that the key is a unique identifier of the squiggle. This configuration of the database allows more efficient access and deletion of data records without the additional overhead of using a relational database, such as SQL. Particularly in cases where the number of data records and length of stored squiggles is small such that the entire database fits into RAM 112.

In one example, an interface software is installed on computer system 103 that communicates with interface electronics 106, such as MinKnow for the MinION device. This interface software may comprise a hardware driver to communicate with interface electronics 106, as well as basic processing functionalities. The interface software may also offer an application programming interface (API) that allows a third party application to access some of the functions provided by the interface software. For example, the interface software receives the stream of sequencing data and writes the data to files on the hard disk 113. Using the API, a third party application can read the stream directly as it is being received and perform the method described above. The API may also offer a function call for ejecting the current read out of the nanopore to skip the remainder of the current read and move on to the next read.

It is noted that the database 114 of stored sequences and their associated counts can be saved to non-volatile memory 113 or uploaded to a remote location over a network at regular or sporadic intervals during the sequencing run. This enables parallel processing of the sequences and their associated counts by processor 110 or an external program during the data acquisition. This can be of benefit if the external process determines that sufficient qualitative or quantitative information has been obtained, which can then be used as a signal to abort the sequencing experiment and economise time, reagents, or resources. Such an application is facilitated by the intrinsic reduction in data (with minimal loss of information) generated by the proposed method.

As described above the proposed method operates on a stream of data, such as nucleotide or peptide sequences from a high-throughput sequencing machine, a file, or standard input. It reads individual sequences or subsequences as they are generated or received, and indexes them 'on the fly' into an appropriate data structure (dictionary or hash table with a key and value, hereafter referred to as the "Index"). If the Index is empty (first read), the sequence, signal or subset thereof is stored in the Index, as well as a separate output file containing the full sequence information. As the streaming progresses, new data is compared to all existing entries in the Index (or a subset thereof) using a comparative similarity function, e.g. dynamic time warping for signal data (ONT).

In the example described above where the streaming data comprises base-space data (also referred to as character data), sequence alignment or indexing tools can be used, such as Needleman-Wunsch, BWA BLAST, or Simrank to determine a matching score of the stream of data against each of the sequences in the database 114. More particularly, sequence alignment and comparison tools provide an alignment or similarity score that can be readily used as the matching score in the methods described herein. It is noted that the matching score may be negative, which means that the matching threshold may also be a negative number. For example, the matching score exceeding the matching threshold may occur when the matching score changes from −10 to −9 for a threshold of −10.

If the sampled sequence or signal compares favourably with en existing entry—based on a predefined similarity threshold obtained from empirical data—the associated key in the Index has its value incremented. If the value is above a user defined saturation threshold, then a termination signal is sent to the acquisition mechanism (409 in FIG. 4) for that single molecule or read, such as reversing the flow of ionic current in Oxford Nanopore Technologies sequencers.

The full sequence information is not saved in this case, but the Index value is incremented nonetheless. Computational complexity can be reduced by restricting the comparisons to the most abundant molecules, which is determined based on the abundance distribution after an initial acquisition period. In some biological systems, a small group of molecules make up the majority of a sample. For example, it has been show that 35% of all RNAs in the human transcriptome are represented by 1% of the population (Clark et al. 2015 Nature Methods). These highly abundant molecules are quickly identified and can be used to populate a small database against which subsequent comparisons can be made to determine whether a sequence is retained or rejected, thus saving memory and time requirements when contrasted to the iterative, full database comparison strategy.

The following disclosure provides one example of pseudocode that can be used to implement the above method Insertion Algorithm
Input
Record "record" that is a dictionary with a sequence value and a key
Output Pre-Conditions
There exists
a dictionary R that stores reads which have not exceeded the count threshold
each entry consists of {sequence name: (sequence, count)} values
a dictionary ER that stores reads which have exceeded the count threshold
each entry consists of {sequence name: (sequence, count)} values
a threshold value ST that represents the saturation threshold (max amount of matches)
a threshold value MT that represents the match threshold
Post-Conditions
Either r or er will have a new entry or they will be unchanged

```
1   if R is empty( ) and ER is_empty( ) then
2       R[record.key] <- record.sequence
3   else
4       match, score, partition <- match algorithm {insert match algorithm here; where partition is R xor ER returned from the match algorithm}
}
5       if score <= MT then
6           partition.count <- partition.count + 1
7           if partition.count > ST
8               reject_read
9           endif
10      else
11          R[record.key] <- record.sequence
12      endif
13  endif
```

Match Execution Algorithm
Input
Record "record" that is a dictionary with a sequence value and a key
Output
String entry name
Int
match score
Reference to the partition that the match came from
Pre-Conditions
There exists
a dictionary r that stores reads which have not exceeded the count threshold
a dictionary er that stores reads which have exceeded the count threshold
a list result that holds the match algorithm scores
Post-Conditions
Either r or er will have a new entry or they will be unchanged

```
1   if R is_empty( ) then
2       partition <- R
3   else
4       partition <- ER
5
6   for entry in partition
7       result.append({score from match algorithm})
8
9   return entry, min(result), partition
```

Figure 4:
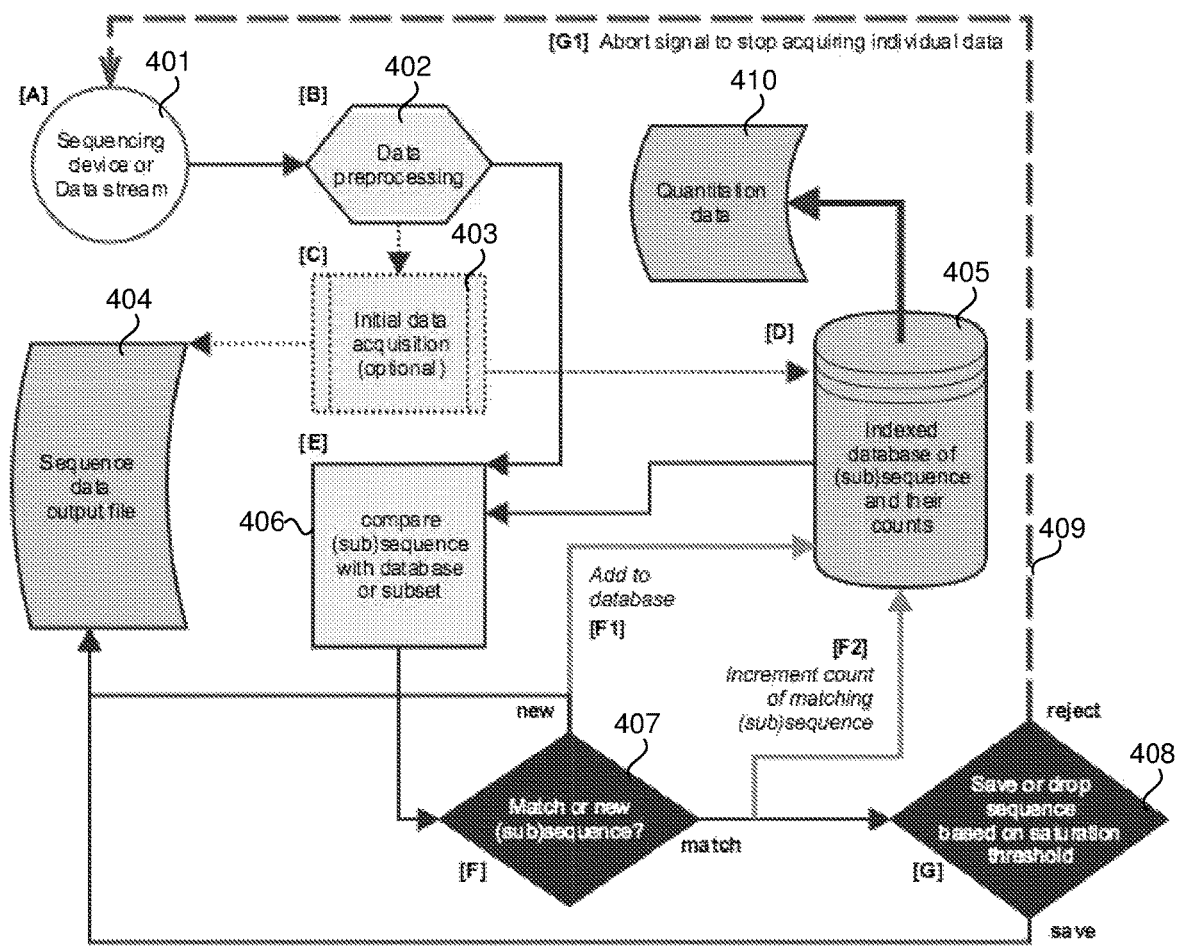
FIG. 4 illustrates one example of how the proposed method can be implemented.

FIG. 4 illustrates one example of how the proposed method can be implemented. This implementation commences by receiving 401 the data stream, followed by data preprocessing 402. At the beginning of the process there may be the step of initial data acquisition 403 that writes the initial data to a sequence data output file 404 and a database 405. Once the initial data acquisition is completed, the next step is to compare 406 the sequence or sub-sequence with the database 405 or subset of database 405 as describe above. A decision 407 is then made on whether there is a match or the sequence is new. If the sequence is new, the processor adds the sequence to database 405. If there is a match 408, the processor saves the sequence if the counter for that sequence in the database is below the saturation threshold or drops the sequence if the counter for that sequence in the database is above the saturation threshold. Saving the sequences involves writing the sequence to the sequence data output file 404. Saving the unique sequence counts and their associated sequence or subsequence involves writing the database 114 to the quantitation data output file 410.

EXPERIMENTS

A prototype implementation of the SQUIDseq algorithm was tested on Oxford Nanopore Technologies RNA sequencing data that had been previously generated using a cDNA strand switch protocol on a R9 flow cell (MCF7 human breast cancer cells). We selected 5000 sequencing reads at random as input (401 in FIG. 4) and subjected them to steps [402, 403, 406, 407, 408]. When a read was rejected in step [409], we emulated an acquisition termination event (or current reversal for ONT sequencers) by adding an additional sequencing read to the input, effectively increasing the sampling by one read. This rejection-prompted, additional input acquisition was reiterated until 5000 sequences were output with SQUIDseq—an equivalent amount to the prior art method.

We compared the event (normalised ionic signal) data contained in the standard fast5 files generated by the MinION sequencer and associated MinKnow software interface for 250 early events (sequential event positions 50-300) from the squiggle of each input read to all existing entries in the database [405] using a dynamic time warping pairwise comparison algorithm. The match threshold, used to determine the similarity cutoff to any previously indexed (sub) sequence, was calibrating using 50 sequencing reads from 5 synthetic RNAs. We used an arbitrary saturation threshold of 150 (sub)sequences, ensuring that no more than 150 full length sequences are output for one Index.

With these parameters, SQUIDseq sampled 54.2% more sequences than the standard sequencing method. Moreover, 242 sequences were sampled with SQUIDseq that would have been ignored otherwise; a 39.3% increase. In its current pre-beta software version, each comparison to an index element takes 0.004 seconds on an Intel i7 2.6 GHz processor, on average.

Figure 5:
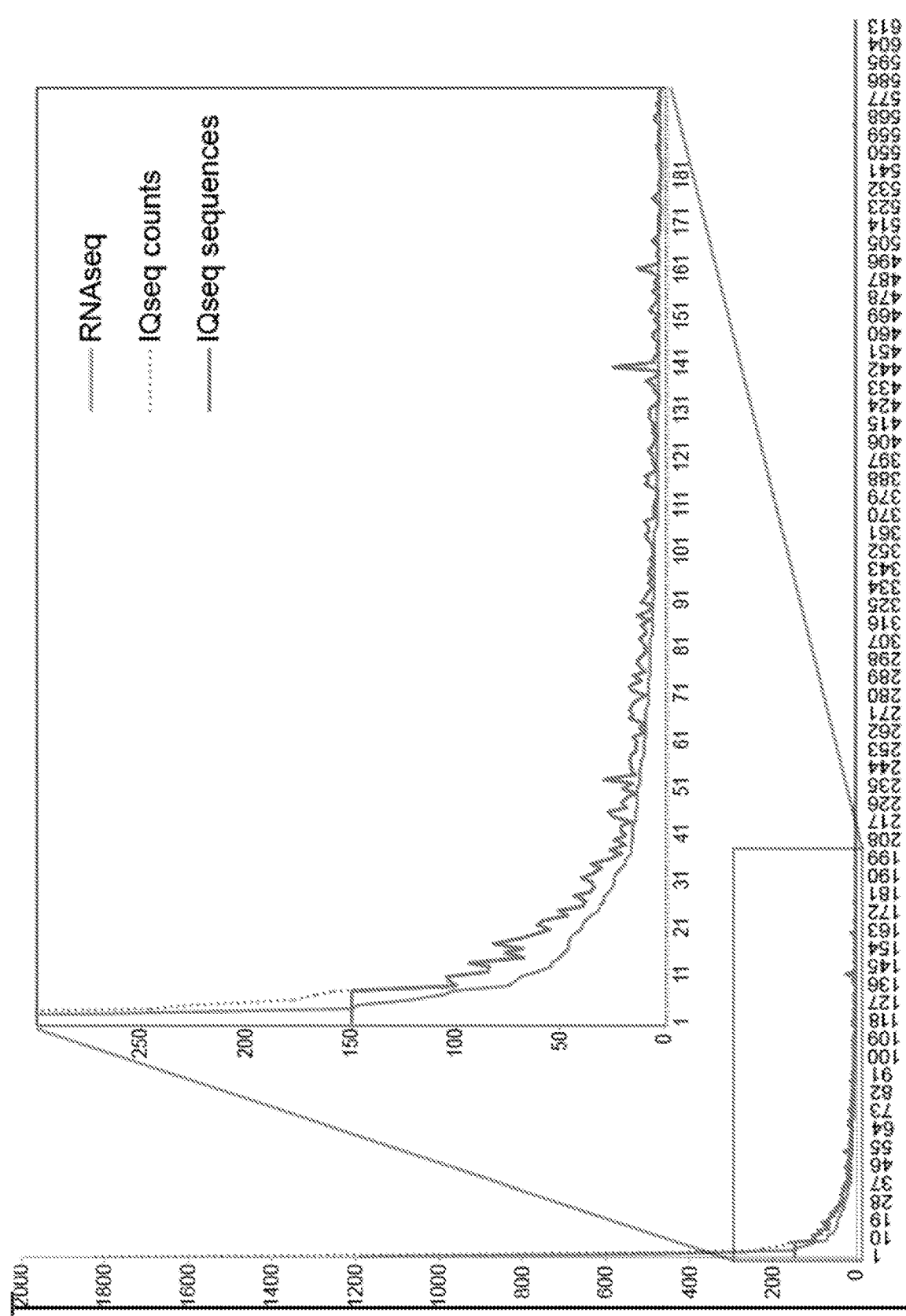
FIG. 5 illustrates a graph showing the number of reads (y-axis) for each sequence (x-axis).

FIG. 5 illustrates a graph showing the number of reads (y-axis) for each sequence (x-axis) where the sequences are ordered by abundance. It can be seen that about the eight most abundant sequences, the number of reads is constant at 150, which is the saturation threshold in this example.

FIG. 6a illustrates the result that the proposed method (SQUIDseq) processes more reads than RNAseq. FIG. 6b illustrates the result that the proposed method (SQUIDseq) locates more unique sequences than RNAseq. FIG. 6c illustrates the coverage (indexed sequence counts) for particular sequences using RNAseq and SQUIDseq, which shows that the coverage using the proposed method is consistently higher. FIG. 6d illustrates the average processing times. In particular, FIG. 6d shows temporal performance of an implementation of the above method including the average time to compare one sequence against a database of 1k, 5k, 10k and 25k stored sequences shown as white boxes, and a comparison of average DTW speedups with default DTW shown as black boxes. It can be easily seen that the proposed method provides a significant reduction in processing times, which allows the sequencing of higher depth for less abundant reads while keeping the sequencing time constant.

The benefits of the proposed method include:
Deeper sampling in applications with limited sampling time
Smaller output data with limited redundancy
Adjustable similarity and saturation thresholds
Real time quantification of sequences or subsequences It will be appreciated by persons skilled in the art that numerous variations and/or modifications may be made to the specific embodiments without departing from the scope as defined in the claims.

It should be understood that the techniques of the present disclosure might be implemented using a variety of technologies. For example, the methods described herein may be implemented by a series of computer executable instructions residing on a suitable computer readable medium. Suitable computer readable media may include volatile (e.g. RAM) and/or non-volatile (e.g. ROM, disk) memory, carrier waves and transmission media. Exemplary carrier waves may take the form of electrical, electromagnetic or optical signals conveying digital data steams along a local network or a publically accessible network such as the internet.

It should also be understood that, unless specifically stated otherwise as apparent from the following discussion, it is appreciated that throughout the description, discussions utilizing terms such as "estimating" or "processing" or "computing" or "calculating", "optimizing" or "determining" or "displaying" or "maximising" or the like, refer to the action and processes of a computer system, or similar electronic computing device, that processes and transforms data represented as physical (electronic) quantities within the computer system's registers and memories into other data similarly represented as physical quantities within the computer system memories or registers or other such information storage, transmission or display devices.

The present embodiments are, therefore, to be considered in all respects as illustrative and not restrictive.

The invention claimed is:

1. A method for processing streaming data from a sequencer, the method comprising:
    receiving multiple sequences from the sequencer, the sequences being indicative of molecules from a biological system;
    storing each of the multiple sequences as data records on a database, each of the multiple sequences being associated with a counter indicative of a number of times the associated sequence has been sequenced;
    progressively receiving a further sequence as streaming data from the sequencer;
    while receiving the further sequence, matching the streaming data against each of the multiple sequences in the database to determine a matching score for each of the multiple sequences in the records of the database;
    upon the matching score exceeding a matching threshold for one of the multiple sequences in the database, selecting the one of the multiple sequences in the database based on the matching score;
    storing the further sequence on non-volatile memory where the counter value associated with the selected sequence is below a saturation threshold; and
    terminating the receiving of the further sequence where the counter value associated with the selected sequence is above the saturation threshold, wherein terminating the receiving of the further sequence comprises sending a reject signal to the sequencer to abort sequencing the further sequence before the sequencer reaches the end of the further sequence and to allow a next sequence to be sequenced before the further sequence is fully sequenced.

2. The method of claim 1, wherein storing the sequence as data records in the database is conditional on the matching score being below the matching threshold for the sequences stored in the database.

3. The method of claim 1, wherein storing the sequence as data records in the database comprises storing a digital representation of an electric signal received from the sequencer.

4. The method of claim 3, wherein matching the streaming data comprises matching a digital representation of an electric signal indicative of the further sequence against the digital representation of the electric signal stored on the database.

5. The method of claim 4, wherein determining a matching score comprises performing dynamic time warping.

6. The method of claim 5, wherein performing dynamic time warping comprises selectively calculating cells in an associated dynamic programming matrix that are within a specified range or value.

7. The method of claim 1, further comprising upon the matching score exceeding a matching threshold for one of the multiple sequences in the database incrementing the counter for the one of the multiple sequences.

8. The method of claim 1, wherein matching the streaming data comprises matching the streaming data against a subset of the multiple sequences in the database, wherein the subset is based on the counter.

9. The method of claim 8, wherein the subset includes sequences for which the associated counter is above an abundance threshold.

10. The method of claim 1, wherein the sequencer comprises a nanopore.

11. The method of claim 1, further comprising:
    monitoring the counters in the database to determine whether one or more counters exceed a depth threshold; and
    upon determining that one or more counters exceed a depth threshold, creating an alert that sufficient sequences have been sequenced.

12. The method of claim 1, wherein the data records form an associative array, each record comprises a key/value pair and the value comprises the sequence and the counter.

13. The method of claim 1, wherein receiving the multiple sequences comprises using an application programming interface (API) to receive the multiple sequences.

14. The method of claim 1, wherein storing the sequence as data records in the database comprises storing a digital representation of a nucleic acid sequence.

15. The method of claim 14, further comprising performing base calling on the further sequence while receiving the further sequence.

16. The method of claim 15, wherein determining the matching score comprises performing sequence alignment or comparison.

17. A computer system for processing streaming data from a sequencer, the computer system comprising:
    a data port to receive multiple sequences from the sequencer, the sequences being indicative of molecules from a biological system;
    a database to store each of the multiple sequences as data records on a database, each of the multiple sequences being associated with a counter indicative of a number of times the associated sequence has been sequenced;
    a processor to:
        while progressively receiving a further sequence as streaming data from the sequencer, match the streaming data against each of the multiple sequences in the records of the database to determine a matching score for each of the multiple sequences in the records of the database
        upon the matching score exceeding a matching threshold for one of the multiple sequences in the database, select the one of the multiple sequences in the database based on the matching score;
        store the further sequence on non-volatile memory where the counter value associated with the selected sequence is below a saturation threshold; and
        terminate the receiving of the further sequence where the counter value associated with the selected sequence is above the saturation threshold, wherein terminating the receiving of the further sequence comprises sending a reject signal to the sequencer to abort sequencing the further sequence before the sequencer reaches the end of the further sequence and to allow a next sequence to be sequenced before the further sequence is fully sequenced.

* * * * *